US012605050B2

(12) United States Patent
Starkweather et al.

(10) Patent No.: US 12,605,050 B2
(45) Date of Patent: Apr. 21, 2026

(54) ENDOSCOPIC DEVICE AND METHODS OF USE THEREOF

(71) Applicant: DRAGONFLY ENDOSCOPY LLC, Englewood, CO (US)

(72) Inventors: Jeremy Starkweather, Englewood, CO (US); Christen Springs, Englewood, CO (US); John Wynne, Englewood, CO (US); Jason Ylizarde, Englewood, CO (US); Amir Govrin, Englewood, CO (US); Doron Katzir, Englewood, CO (US)

(73) Assignee: Dragonfly Endoscopy LLC, Englewood, CO (US)

( * ) Notice: Subject to any disclaimer, the term of this patent is extended or adjusted under 35 U.S.C. 154(b) by 552 days.

(21) Appl. No.: 17/421,578

(22) PCT Filed: Jan. 10, 2020

(86) PCT No.: PCT/US2020/013205
§ 371 (c)(1),
(2) Date: Jul. 8, 2021

(87) PCT Pub. No.: WO2020/146812
PCT Pub. Date: Jul. 16, 2020

(65) Prior Publication Data
US 2022/0079419 A1 Mar. 17, 2022

Related U.S. Application Data

(60) Provisional application No. 62/791,497, filed on Jan. 11, 2019.

(51) Int. Cl.
*A61B 1/005* (2006.01)
*A61B 1/00* (2006.01)
(Continued)

(52) U.S. Cl.
CPC ........ *A61B 1/0052* (2013.01); *A61B 1/00016* (2013.01); *A61B 1/0057* (2013.01);
(Continued)

(58) Field of Classification Search
CPC . A61B 1/0052; A61B 1/00016; A61B 1/0057; A61B 1/008; A61B 1/015;
(Continued)

(56) References Cited

U.S. PATENT DOCUMENTS 7,465,288 B2 12/2008 Dudney et al.
7,691,095 B2 4/2010 Bednarek et al.
(Continued)

FOREIGN PATENT DOCUMENTS

CN 102469916 A 5/2012
CN 103889299 A 6/2014
(Continued)

OTHER PUBLICATIONS

Japanese Office Action issued in Japanese Patent Application No. 2021-540327, dated Aug. 6, 2024, 2 pages.
(Continued)

*Primary Examiner* — Michael J Carey
*Assistant Examiner* — Christen A. Sharpless
(74) *Attorney, Agent, or Firm* — BakerHostetler

(57) ABSTRACT
The disclosure provides for an endoscopic device and method for manipulating the endoscopic device. The endoscopic device includes a tube assembly and a slider mechanism connected to the cylindrical body for control of the endoscopic device. The tube assembly has a cylindrical body with a proximal end and a distal end and a plurality of openings extending from the proximal end to the distal end of the cylindrical body. The slider mechanism includes a tip deflecting mechanism and a rotation assembly having a planetary gear system.

28 Claims, 16 Drawing Sheets

(51) Int. Cl.

| | |
|---|---|
| *A61B 1/008* | (2006.01) |
| *A61B 1/015* | (2006.01) |
| *A61B 1/045* | (2006.01) |
| *A61B 1/06* | (2006.01) |
| *A61B 1/273* | (2006.01) |
| *A61M 25/01* | (2006.01) |

(52) U.S. Cl.
CPC .............. *A61B 1/008* (2013.01); *A61B 1/015* (2013.01); *A61B 1/045* (2013.01); *A61B 1/0661* (2013.01); *A61B 1/273* (2013.01); *A61M 25/0147* (2013.01)

(58) Field of Classification Search
CPC ....... A61B 1/045; A61B 1/0661; A61B 1/273; A61B 1/00042; A61B 1/012; A61M 25/0147

See application file for complete search history.

(56) References Cited

U.S. PATENT DOCUMENTS

| | | | |
|---|---|---|---|
| 7,789,826 | B2 | 9/2010 | Sullivan et al. |
| 7,922,650 | B2 | 4/2011 | McWeeney et al. |
| 8,363,097 | B2 | 1/2013 | Kazakevich et al. |
| 8,556,850 | B2 | 10/2013 | Tegg |
| 8,608,649 | B2 | 12/2013 | McWeeney et al. |
| 8,690,756 | B2 | 4/2014 | Deal |
| 8,790,250 | B2 | 7/2014 | Petersen et al. |
| 8,858,495 | B2 | 10/2014 | Tegg et al. |
| 9,162,036 | B2 | 10/2015 | Caples et al. |
| 9,339,173 | B2 | 5/2016 | McWeeney et al. |
| 9,700,699 | B2 | 7/2017 | Morris et al. |
| 9,907,456 | B2 | 3/2018 | Miyoshi |
| 9,931,487 | B2 | 4/2018 | Quinn et al. |
| 10,058,234 | B2 | 8/2018 | Carroux et al. |
| 10,117,567 | B2 | 11/2018 | Okamoto |
| 10,183,149 | B2 | 1/2019 | Tegg et al. |
| 10,617,848 | B2 | 4/2020 | Weitzner et al. |
| 10,632,287 | B2 | 4/2020 | Romoscanu et al. |
| 10,661,057 | B2 | 5/2020 | Davies et al. |
| 10,799,675 | B2 | 10/2020 | Khuu et al. |
| 10,806,896 | B2 | 10/2020 | Davies et al. |
| 10,918,833 | B2 | 2/2021 | Appling et al. |
| 11,064,869 | B2 | 7/2021 | McWeeney et al. |
| 11,364,365 | B2 | 6/2022 | Regnier et al. |
| 11,395,579 | B2 | 7/2022 | Ouyang et al. |
| 11,503,984 | B2 | 11/2022 | Surti et al. |
| 11,654,262 | B2 | 5/2023 | Furnish et al. |
| 12,226,075 | B2 | 2/2025 | Kucharski et al. |
| 2007/0265499 | A1 | 11/2007 | Wood et al. |
| 2009/0138025 | A1* | 5/2009 | Stahler .................. A61B 34/71 |
| | | | 606/130 |
| 2010/0179383 | A1 | 7/2010 | Kosuke et al. |
| 2012/0089125 | A1 | 4/2012 | Scheibe et al. |
| 2012/0089556 | A1 | 4/2012 | Stergiou et al. |
| 2013/0184528 | A1 | 7/2013 | Onuki et al. |
| 2014/0221749 | A1 | 8/2014 | Grant et al. |
| 2014/0316202 | A1* | 10/2014 | Carroux ............ A61B 1/00085 |
| | | | 600/146 |
| 2016/0029875 | A1* | 2/2016 | Okada ................ A61B 1/00101 |
| | | | 600/107 |
| 2016/0174819 | A1* | 6/2016 | Ouyang ............ A61B 1/00098 |
| | | | 600/105 |
| 2017/0290575 | A1 | 10/2017 | Sato |
| 2018/0028212 | A1* | 2/2018 | Akilian .......... A61B 17/320783 |
| 2018/0028778 | A1* | 2/2018 | Dillon .................. A61B 1/0051 |
| 2018/0160883 | A1 | 6/2018 | Viebach et al. |
| 2019/0282071 | A1* | 9/2019 | Ouyang ............ A61B 1/00052 |
| 2019/0374095 | A1* | 12/2019 | Lord ...................... A61B 1/053 |
| 2020/0188640 | A1* | 6/2020 | Palushi ................ A61M 25/10 |
| 2021/0321861 | A1 | 10/2021 | McWeeney et al. |
| 2021/0338052 | A1* | 11/2021 | Ouyang ............ A61B 1/00128 |

FOREIGN PATENT DOCUMENTS

| | | | | |
|---|---|---|---|---|
| CN | 104414737 | A | 3/2015 | |
| CN | 108135445 | A | 6/2018 | |
| CN | 108882832 | A | 11/2018 | |
| DE | 102015116652 | A1 * | 4/2016 | ......... A61B 1/00066 |
| EP | 0705571 | A1 | 4/1996 | |
| EP | 2324755 | B1 | 7/2012 | |
| EP | 2839798 | A1 | 2/2015 | |
| EP | 2517613 | B1 | 10/2016 | |
| EP | 2594308 | B1 | 12/2018 | |
| EP | 3423141 | B1 | 1/2023 | |
| JP | 2005046488 | A | 2/2005 | |
| JP | 2005287576 | A | 10/2005 | |
| JP | 2006116331 | A | 5/2006 | |
| JP | 2007265499 | | 10/2007 | |
| JP | 2007299708 | A | 11/2007 | |
| JP | 2007530155 | A | 11/2007 | |
| JP | 2012089125 | A | 5/2012 | |
| JP | 2014199759 | A | 10/2014 | |
| JP | 2015536192 | A | 12/2015 | |
| JP | 2016002792 | A | 1/2016 | |
| JP | 2016522704 | A | 8/2016 | |
| JP | 2019097907 | A | 6/2019 | |
| JP | 2022513809 | A | 2/2022 | |
| WO | WO 2010002544 | A1 | 1/2010 | |
| WO | WO2014174378 | A1 | 10/2014 | |
| WO | WO2014210088 | A1 | 12/2014 | |
| WO | WO2014070396 | A1 | 5/2025 | |

OTHER PUBLICATIONS

Notice of Allowance issued in Chinese Patent Application No. CN 20208008559.2, mailed Aug. 16, 2024.

* cited by examiner

132

134

106

130

128

126

133

135

120

143

141          141

140          140

120          142

ENDOSCOPIC DEVICE AND METHODS OF USE THEREOF

CROSS-REFERENCE TO RELATED APPLICATIONS

The present application is the National Stage Application of International Patent Application No. PCT/US2020/013205, filed Jan. 10, 2020, which claims priority to and the benefit of U.S. Provisional Patent Application No. 62/791,497, "ENDOSCOPIC DEVICE AND METHODS OF USE THEREOF" (filed Jan. 11, 2019), the entirety of which foregoing applications are incorporated herein by reference in their entirety for any and all purposes.

FIELD

The present disclosure is directed to assemblies for medical devices and methods of use. More particularly, the disclosure relates to endoscopic device assemblies for single hand manipulation of a catheter.

BACKGROUND

Endoscopes provide mechanical support to a variety of endoscopic devices. Endoscopic devices are usually passed through a working channel of the endoscope positioned in a body cavity in order to reach an operative site at a distal end of the endoscopic device.

Multi-endoscope procedures may require more than one operator which can lead to problems associated with coordination, cost, time. Single operator systems may require more than one hand, include non-intuitive controls, or have multiple controls to manipulate the device. Current endoscopic devices lack precise, rotational control of the distal tip, which can make navigation through small or complicated anatomy difficult. Endoscopic devices also require the use of capital equipment for operation, which can be a significant burden financially and/or due to accessibility.

Therefore, there is a need for an intuitive handle assembly that allows for single hand, rotational manipulation of endoscopic devices without the use of capital equipment, among other uses.

SUMMARY

The disclosure provides for an endoscopic device having a tube assembly including a cylindrical body and a slider mechanism. The cylindrical includes a plurality of openings extending from the proximal end to the distal end of the cylindrical body. The slider mechanism is connected to the cylindrical body and includes a rotation assembly and a tip deflecting mechanism. The rotational assembly can include a planetary gear system. In some variations, the planetary gearing system can include one or more rotational stops. In some variations, the planetary gearing system increases or decreases rotation at a ratio from 4:1 to 1:4.

In an aspect, the rotation assembly further includes a knob having an outer surface and an inner surface. In an aspect, the planetary gear system includes a ring gear on the inner surface of the knob. In another aspect, the knob includes a plurality of recessions on the outer surface of the knob. In another aspect, the planetary gear system includes at least two planet gears.

In an aspect, the slider mechanism is configured to rotate around the cylindrical body. In some instances, the slider mechanism is configured to rotate at least 360° around the cylindrical body. In some instances, the slider mechanism is configured to rotate up to and including 200° in a clockwise direction and up to and including 200° in a counterclockwise direction. In further instances, the slider mechanism is configured to rotate up to and including 180° in a clockwise direction and up to and including 180° in a counterclockwise direction.

In certain variations, the tip deflecting mechanism is connected to the distal tip of the catheter by at least one pull wire. In some alternatives, the slider mechanism is configured to rotate up to and including 100° in a clockwise direction and up to and including 100° in a counterclockwise direction. In some alternatives, the slider mechanism is configured to rotate up to and including 90° in a clockwise direction and up to and including 90° in a counterclockwise direction. In further alternatives, the slider mechanism is configured to rotate up to and including 70° in a clockwise direction and up to and including 70° in a counterclockwise direction. In further alternatives, the slider mechanism is configured to rotate up to and including 60° in a clockwise direction and up to and including 60° in a counterclockwise direction.

In an additional aspect, the tip deflecting mechanism is connected to the distal tip of the catheter by at least one pull wire. In some variations, the tip deflecting mechanism is connected to the distal tip of the catheter by at least two pull wires. In further variations, the tip deflecting mechanism is connected to the distal tip of the catheter by at least three pull wires.

In other aspects, the slider mechanism is configured to translate toward the distal end or toward the proximal end of the cylindrical body. The endoscopic device includes a catheter operatively connected to the slider mechanism. In an aspect, the tube assembly further includes at least two ports fluidly connected to the catheter. In some variations, first port of the two ports is fluidly connected to the catheter proximal from the rotational assembly, and the second port of the two ports is fluidly connected to the catheter distal from the rotational assembly. In an additional aspect, the endoscopic device endoscopic device is a cholangioscope.

In another aspect, the endoscopic device includes a light source disposed at the distal end of the catheter. The light source can be operably connected to the proximal end of the catheter through a channel in the catheter. In a further aspect, a working channel can traverse the length of the catheter from the proximal end to the distal end. In a further aspect, one or more pull wire channels can traverse the length of the catheter from the proximal end to the distal end.

In an aspect, the endoscopic device further includes a control assembly comprising a video processor. In various aspects, the control assembly may further include an endoscope attachment, a light source, a wireless transceiver, and/or a battery. The tip deflecting mechanism may be a switch, a lever, or at least one button. In an aspect, the tip deflecting mechanism is powered. In an aspect, the tube assembly and the control assembly are detachably connected with a locking mechanism. In another aspect, the tube assembly and the control assembly are integrally connected.

Further provided herein is a method of manipulating an endoscopic device. The method may include inserting the endoscopic device comprising a catheter through a working channel of an endoscope. In an aspect, the method may further include rotating the rotation assembly around the cylindrical body to rotate the catheter of the endoscopic device. In another aspect, the method may further include translating the slider mechanism toward the distal end or toward the proximal end of the cylindrical body to extend or retract the catheter, respectively. In some aspects, the method further includes engaging a tip deflecting mechanism. In another aspect, the method further includes activating a light source in the control assembly and acquiring a video signal from the distal tip of the catheter. In other aspects, the method may further include processing the video signal with the video processor and transmitting the video signal to an external display. The video signal is transmitted wirelessly using a wireless transceiver in some aspects.

Additional aspects and features are set forth in part in the description that follows, and will become apparent to those skilled in the art upon examination of the specification or may be learned by the practice of the disclosed subject matter. A further understanding of the nature and advantages of the disclosure may be realized by reference to the remaining portions of the specification and the drawings, which forms a part of this disclosure.

BRIEF DESCRIPTION OF THE DRAWINGS

The description will be more fully understood with reference to the following figures, which are presented as variations of the disclosure and should not be construed as a complete recitation of the scope of the disclosure, wherein.

DETAILED DESCRIPTION

The disclosure may be understood by reference to the following detailed description, taken in conjunction with the drawings as described below. It is noted that, for purposes of illustrative clarity, certain elements in various drawings may not be drawn to scale.

For purposes of this description, "distal" refers to the end extending into a body and "proximal" refers to the end extending out of the body.

For purposes of this description, "endoscopic device" refers to medical devices extending into the interior of a hollow organ or cavity of the body. An endoscopic device may be used for flexible endoscopy. In some variations, an endoscopic device may include a mechanical manipulation controller capable of controlling the endoscopic device with 360° rotation and advancement and retraction capabilities.

A "planetary gear system", or epicyclic gear train, includes at least two gears arranged so that the center of one gear revolves around the center of the other. A carrier connects the centers of the two gears and rotates to carry the planet gear around the sun gear. The planet gear may rolls on the inside of the pitch circle of a fixed, outer ring gear, sometimes called an annular gear.

For purposes of this description "connected to" includes two components being directly connected or indirectly connected with intervening components.

Disclosed herein are endoscopic devices having an intuitive handle assembly for manipulating the endoscopic device and methods of use thereof. The disclosed device and method for manipulation provide a simpler and more intuitive way of navigating the tip of a catheter associated with the endoscopic device. For example, the endoscopic device may provide for single handed, rotational manipulation of the device. Also disclosed herein are endoscopic devices that are single use and do not require capital equipment. For example, the endoscopic device may include an integrated microprocessor, light source, and/or power source which eliminate the need for endoscopic capital equipment. In other examples, the endoscopic device may include minimal capital equipment that is smaller and more portable than standard endoscopic capital equipment. The endoscopic device may connect to or work in conjunction with another endoscope, thus allowing a "plug-and-play" adaptation to existing endoscopes. Thus, the endoscopic device may be adaptable to be used with existing endoscopes without any additional equipment.

Figure 1:
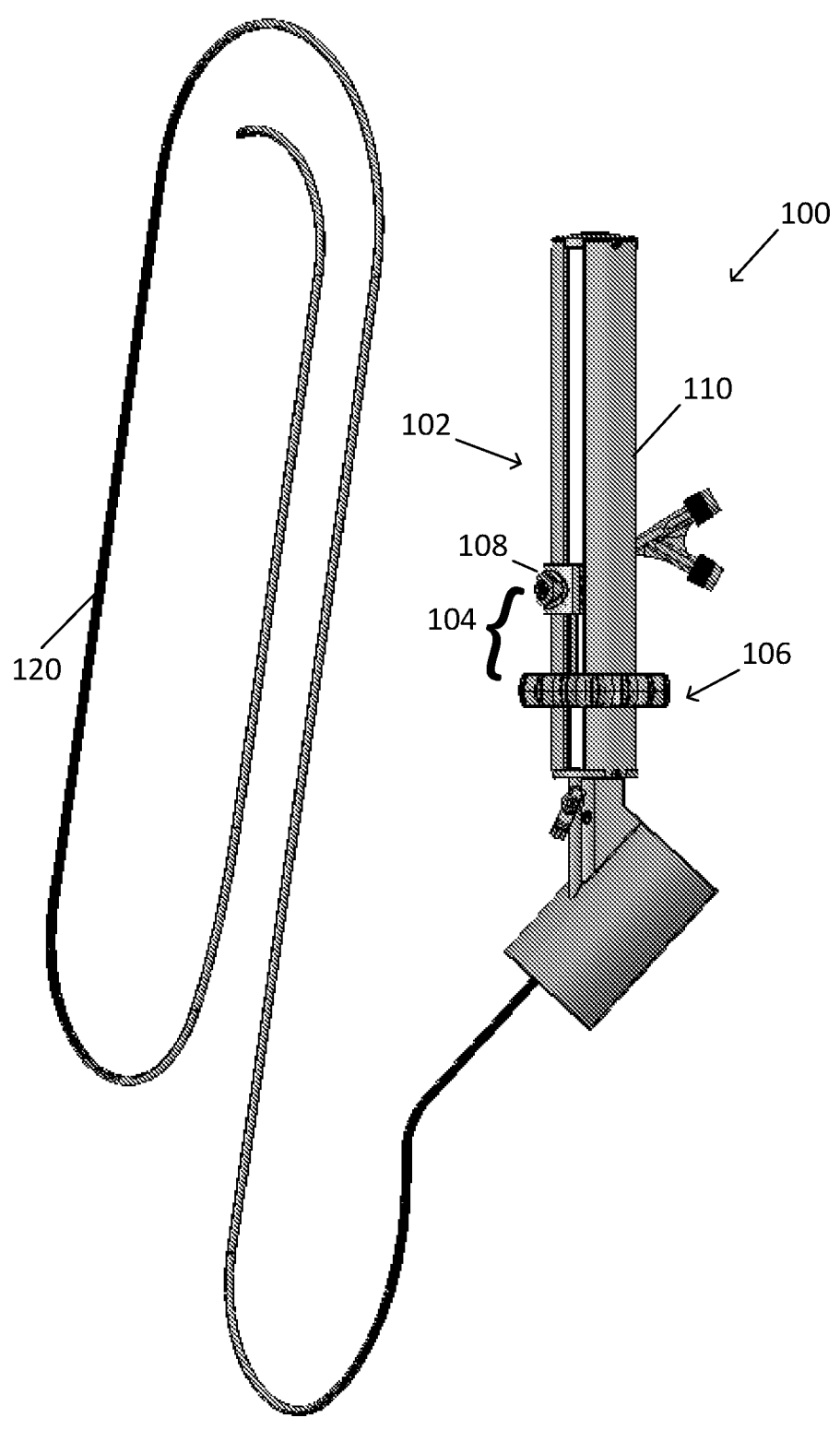
FIG. 1 is a view of the endoscopic device with tube assembly, control assembly, and catheter in one variation.

As seen in FIG. 1, the endoscopic device 100 may include a tube assembly 102 having a cylindrical body 110 and a slider mechanism 104 connected to the cylindrical body. In a variation, the endoscopic device 100 may further include a control assembly attached to the cylindrical body and a catheter that extends through the control assembly and connects to the slider mechanism. In a variation the tube assembly and the control assembly may be detachably connected. In another variation, the tube assembly and the control assembly may be integral. For example, the tube assembly and the control assembly may not be separated or the control assembly may be located within the tube assembly. Catheter ports may then fluidly connect to the catheter and attach to the slider mechanism.

Figure 2:
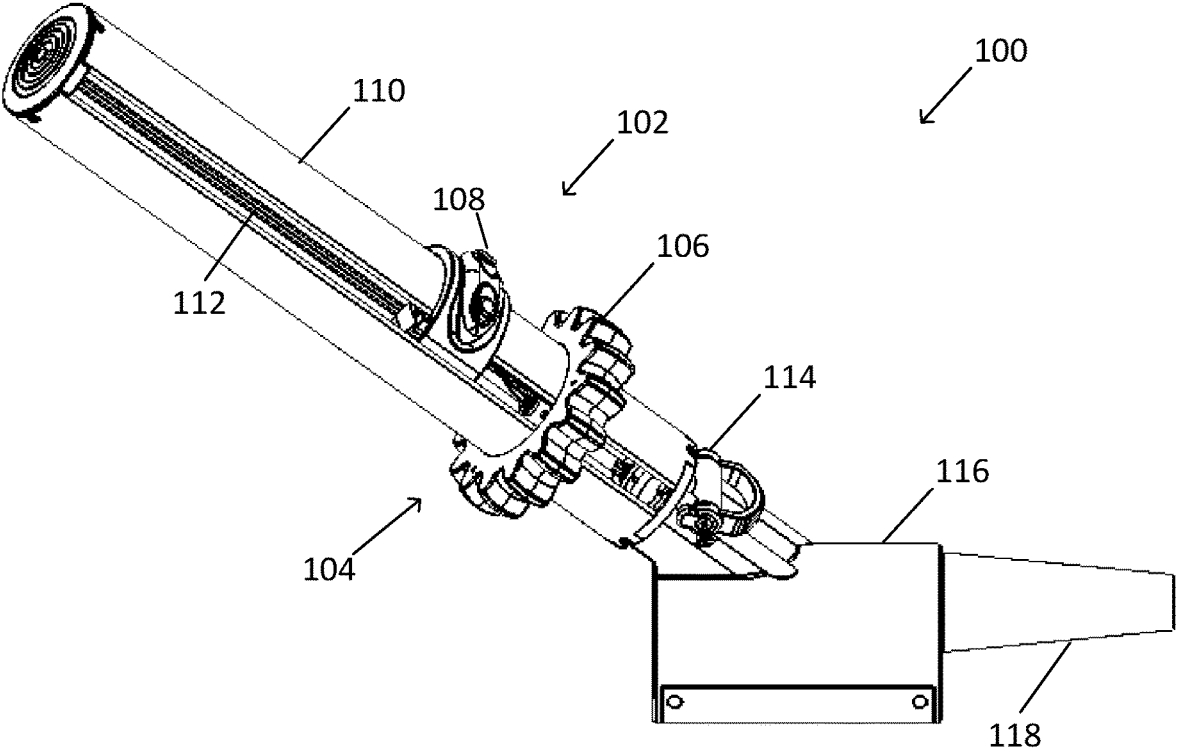
FIG. 2 is a view of the endoscopic device with tube assembly and control assembly with endoscope attachment in one variation.
Figure 3A:
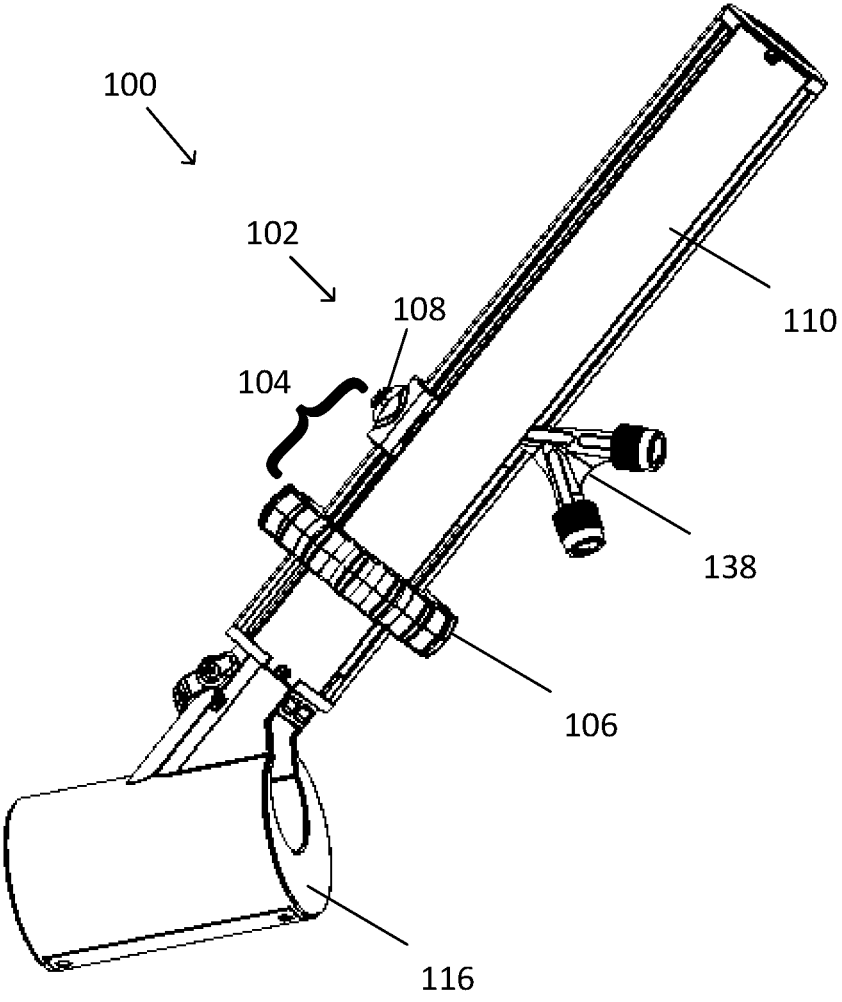
FIG. 3A is a view of the endoscopic device with tube assembly and control assembly without an endoscope attachment and with a Y-connector in one variation.
Figure 3B:
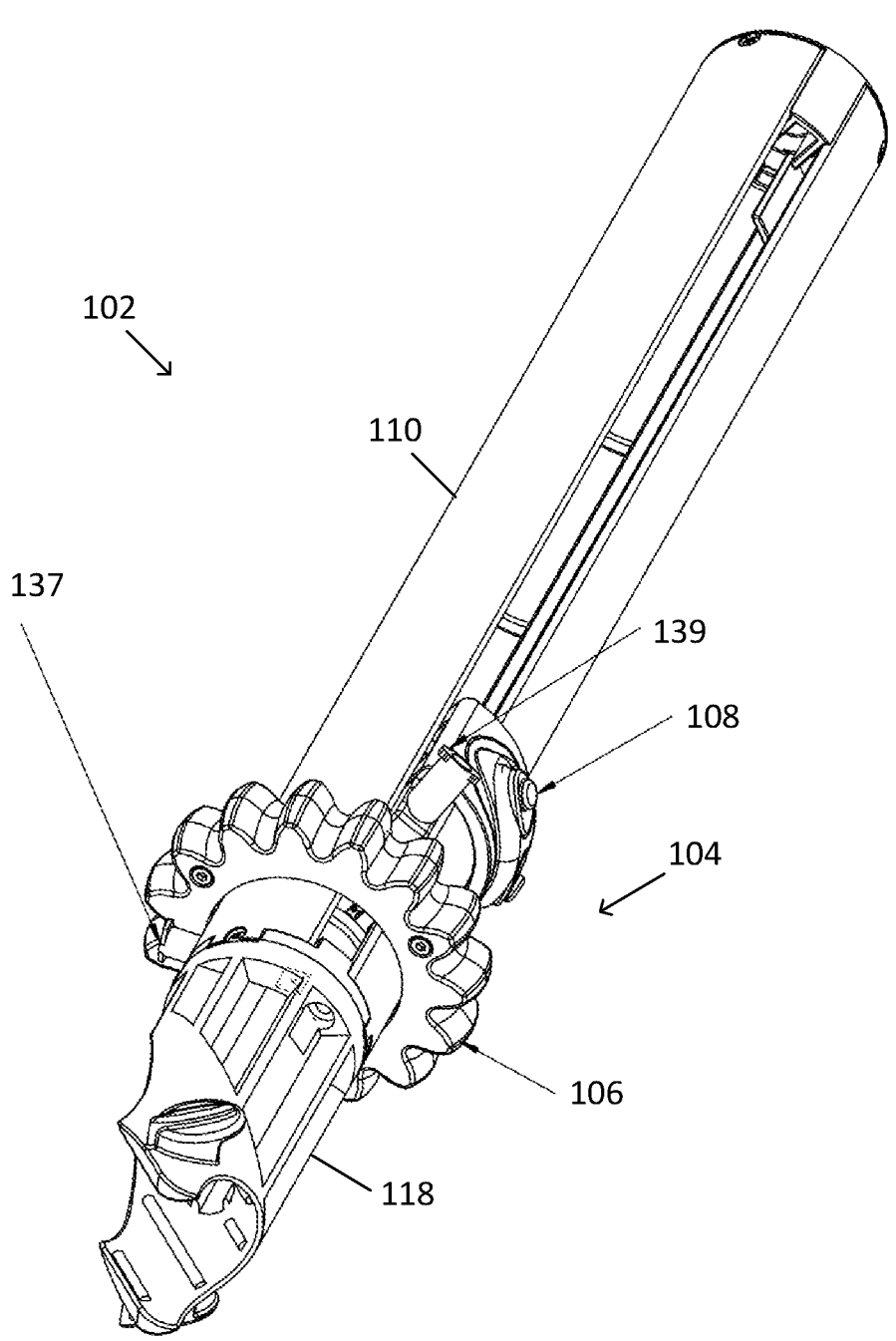
FIG. 3B is a view of the tube assembly with two separated ports in one variation.
Figure 7:
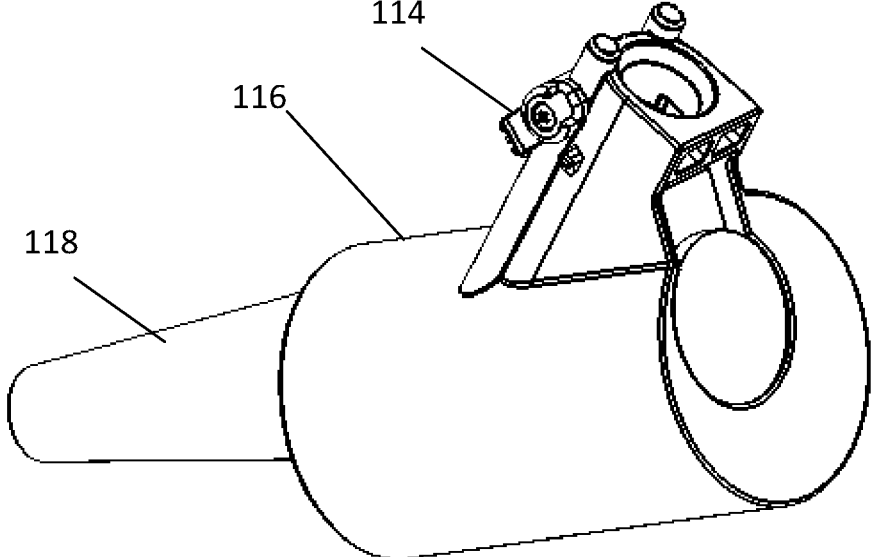
FIG. 7 is a view of the control assembly in one variation.

FIG. 2 illustrates one variation of the endoscopic device 100 with a tube assembly 102 (FIG. 4), a control assembly 116 (FIG. 7), and an endoscope attachment 118 (FIGS. 2, 3B, and 7). The endoscope attachment 118 is configured to connect the endoscopic device to a larger endoscope. In one variation, the larger endoscope is a duodenoscope. For example, the endoscope attachment 118 may align the entry port of the larger endoscope with the working channel of the endoscopic device. In one variation, the endoscope attachment may be conical, tapered, or any shape capable of connecting to an entry port of the larger endoscope. In some variations, the control assembly 116 is connected to an endoscope attachment 118, as depicted in FIG. 2. In other variations, the control assembly is not directly connected to the tube assembly, and the endoscope attachment 118 is directly connected to the distal end of the cylindrical body 110 of the tube assembly 102, as depicted in FIG. 3B. FIG. 3A illustrates a variation of the endoscopic device 100 with a tube assembly 102 and a control assembly 116, where the control assembly does not include an endoscope attachment.

The endoscope attachment may be directly coupled to the entry port of the larger endoscope channel. The endoscope attachment may further provide a seal at the entry port to prevent bodily fluids leaving the endoscope and maintain positive or negative pressure in the lumen of the endoscope. In some variations, the endoscope attachment 118 may be a screw fit attachment, a snap fit attachment, a press fit attachment, or a compression fit attachment, without limitation.

Figure 4:
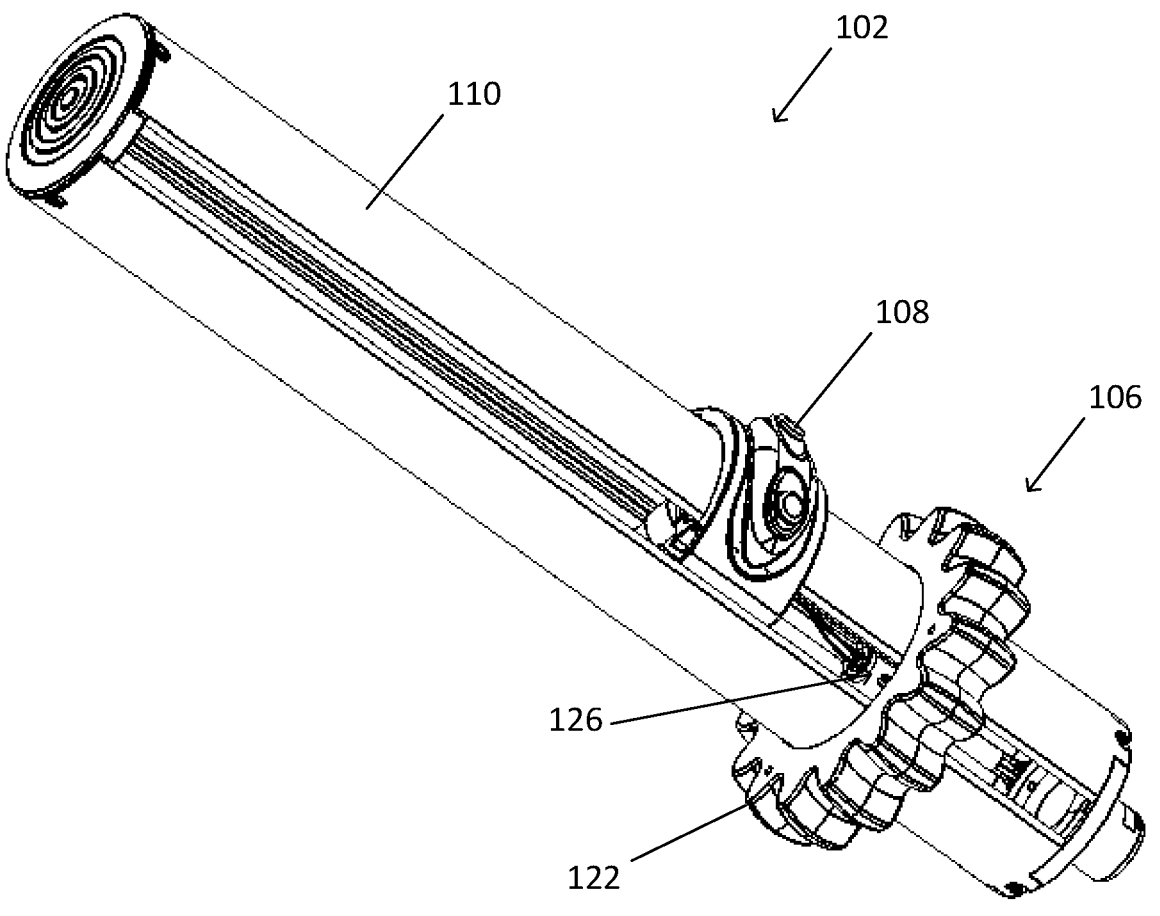
FIG. 4 is a view of the tube assembly in one variation.

As seen in FIGS. 3A, 3B, and 4, the tube assembly 102 includes the cylindrical body 110 and the slider mechanism 104 (including the rotation assembly 106 and the tip deflecting mechanism 108). The cylindrical body 110, as further seen in FIG. 5A, may have a proximal end and a distal end and include a plurality of openings 112 extending the length of the cylindrical body 110, from the proximal end to the distal end. In a variation, the openings may be vertical, as the cylindrical body is held in a vertical orientation for operation. The vertical openings may have a 90% tolerance. In some variations, the cylindrical body may have at least 2 openings. In some variations, the cylindrical body may have at least 3 openings. In some variations, the cylindrical body may have at least 4 openings. In some variations, the cylindrical body may have at least 5 openings. In some variations, the cylindrical body may have at least 6 openings. The openings may be symmetrically located around the circumference of the cylindrical body. The number of openings and size of the openings may correspond with the number and size of the arms used in the planetary gear system as discussed below. In one variation, the width of each opening is the diameter of at least one of the planet gears.

The slider mechanism 104, as further seen in FIGS. 5B and 7A-7C, may include a rotation assembly 106 comprising a planetary gear system 124 and a tip deflecting mechanism 108. In one variation, the slider mechanism 104 includes a rotation assembly 106 operatively connected to a tip deflecting mechanism 108. Referring back to FIG. 1, the slider mechanism 104 provides for a user to manipulate the movement of a catheter 120 operatively connected to the slider mechanism. In particular, the rotation assembly 106 provides for the rotation of the catheter 120, the tip deflecting mechanism 108 provides for the deflection of the tip of the catheter 120, and the entire slider mechanism 104 (the rotation assembly and the tip deflecting mechanism) can be translated along the cylindrical body 110 to provide for advancement or retraction of the catheter 120. The slider mechanism 104, by way of the rotation assembly 106, is configured to rotate around the cylindrical body 110. This results in rotational control of the tip of the catheter 120. The manipulation of the endoscopic device may be intuitive such that manipulation of the slider mechanism manipulates a catheter attached to the slider mechanism in a similar manner. For example, rotation of the rotation assembly to the right rotates the catheter tip to the right. Similarly, translation of the slider mechanism towards the proximal end of the cylindrical body retracts the catheter tip by a same or similar distance as the translation. Therefore, the slider mechanism allows for intuitive control of the catheter, including tip deflection and retraction/advancement.

Figure 6A:
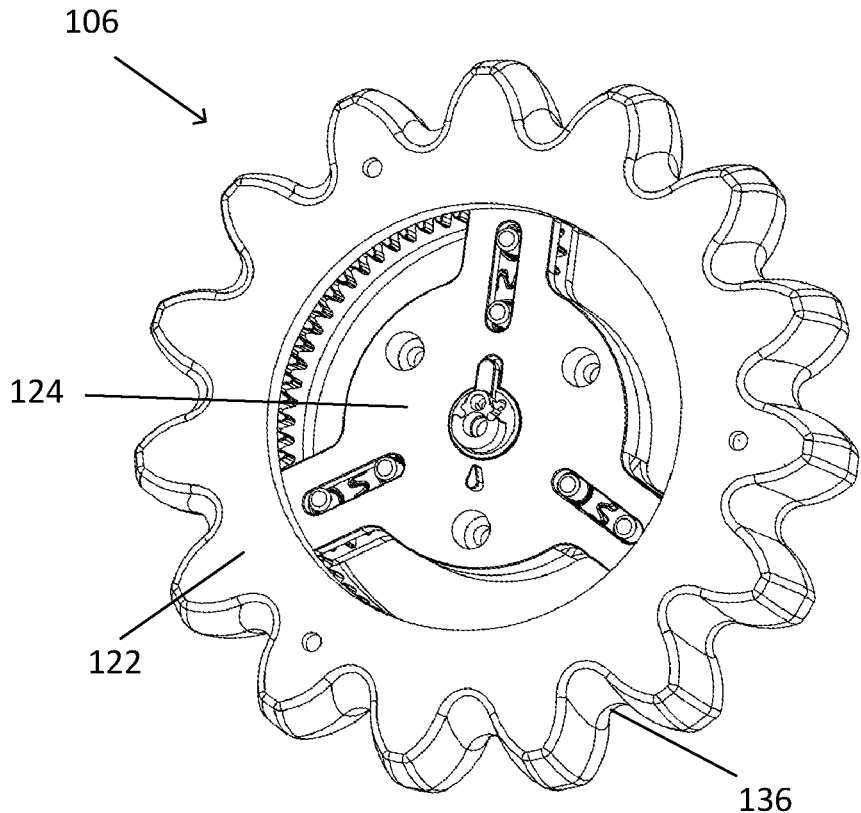
FIG. 6A is a view of the rotation assembly in one variation.
Figure 6B:
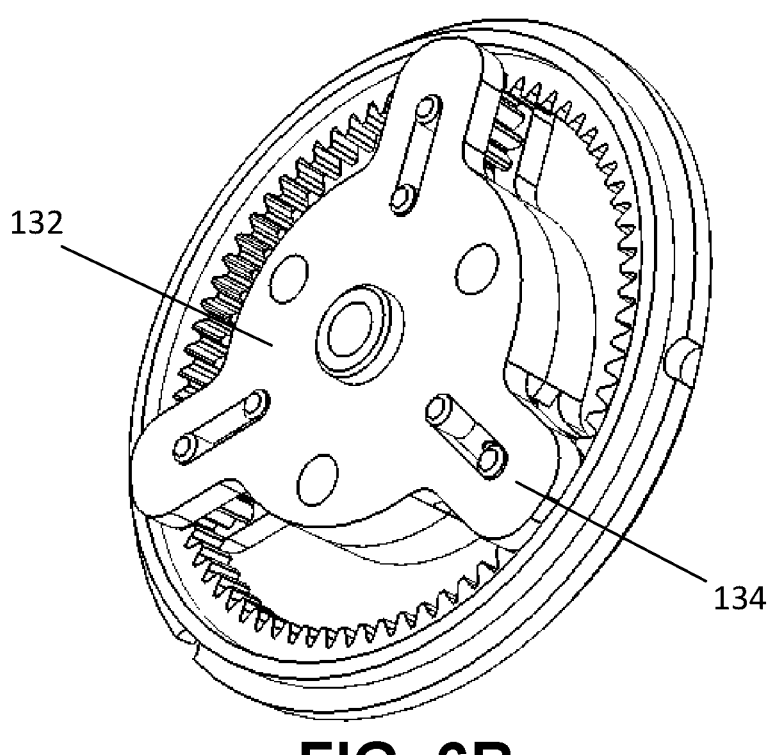
FIG. 6B is a view of the planetary gear system in one variation.
Figure 6C:
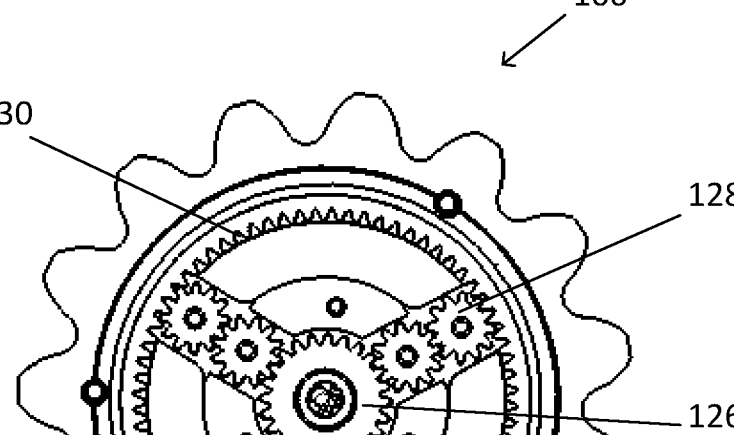
FIG. 6C is a top view of the rotation assembly in one variation.

The rotation assembly 106 includes, but is not limited to, a knob 122 having an outer surface and an inner surface and a planetary gear system 124. As seen in FIGS. 6B and 6C, the planetary gear system 124 may include a sun gear 126, at least two planet gears 128, and a ring gear 130, such that the planet gears 128 are located between the central sun gear 126 and the surrounding ring gear 130. In a variation, the sun gear, planet gears, and ring gear axes are coaxial. The planetary gear system 124 may further include a carrier 132 for holding the planet gears 128. In a variation the carrier may have at least two arms 134 configured to hold the at least one planet gear 128. In one variation, each arm 134 may be configured to hold two planet gears 128. In a variation, the carrier 132 may have at least 3 arms. In a variation, the carrier 132 may have at least 4 arms. In a variation, the carrier 132 may have at least 5 arms. In a variation, the carrier 132 may have at least 6 arms. The arms 134 are symmetrical around the sun gear and extend from the ring gear to the sun gear. In some variations, the planetary gear system comprises at least 2 planet gears. In some variations, the planetary gear system includes at least 3 planet gears. In some variations, the planetary gear system includes at least 4 planet gears. In some variations, the planetary gear system includes at least 5 planet gears. In some variations, the planetary gear system includes at least 6 planet gears. In some variations, the planetary gear system includes, at least 7 planet gears. In some variations, the planetary gear system includes at least 8 planet gears. In some variations, the planetary gear system includes at least 9 planet gears. In some variations, the planetary gear system includes at least 10 planet gears.

In a variation, the planetary gear system 124 is a double-pinion planetary gear system. In this variation, the planetary gear system includes two meshed planet gear sets between the sun gear and the ring gear. An arm of the carrier may hold an outer planet gear and an inner planet gear at different radii from the sun gear centerline, and allow the individual planet gears to rotate with respect to each other. For example, the planetary gear system in FIGS. 6A-6C includes 3 sets of meshed planet gear sets, each with an outer planet gear and an inner planet gear.

The size of the planetary gear system 124 may vary based on the size of the cylindrical body. In some variations, the size of the gears in the planetary gear system varies with the application of the endoscopic device. In general, the relationship between the gears in a double-pinion planetary gear system may be represented by Eqn. 1.

$$r_r = r_s + 2 \cdot r_{pi} + 2 \cdot r_{po}, \qquad \text{Eqn. 1}$$

where: $r_r$ is the ring gear radius, $r_s$ is the sun gear radius, $r_{pi}$ is the inner planet gear radius, and $r_{po}$ is the outer planet gear radius. In a variation, the inner planet gear and the outer planet gear are the same size. In another variation, the inner planet gear and the outer planet gear are different sizes.

The ring gear may have a radius ranging from about 2 mm to about 20 mm. In a variation, the ring gear may have a diameter of at least 4 mm. In a variation, the ring gear may have a diameter of at least 6 mm. In a variation, the ring gear may have a diameter of at least 10 mm. In a variation, the ring gear may have a diameter of at least 20 mm. In a variation, the ring gear may have a diameter of at least 30 mm. In a variation, the ring gear may have a diameter of at least 40 mm.

In a variation, the planet gears 128 are held stationary and the ring gear 130 is used as an input. If there is one planet gear between ring gear and the sun gear, the ring gear and the sun gear will rotate in opposite directions. For example, if the ring gear is turned clockwise, then the sun gear will turn counterclockwise. The double-pinion planetary gear system reverses the relative rotation directions of the ring and sun gears. Therefore, meshed planet gear sets in the double-pinion planetary gear system allow the rotation of the ring gear to be in the same direction as the rotation of the sun gear. Therefore, when the ring gear is rotated, the sun gear will rotate in the same direction. In one variation, the rotation assembly includes a double-pinion planetary gear system such that rotation of the ring gear results in rotation of the sun gear, and anything attached thereto, in the same direction. For example, in some variations, a catheter may be attached to the sun gear so that the catheter is rotated based on the rotation of the ring gear. The ring gear, the sun gear, and the planet gears may rotate up to 360°.

In a variation, the planetary gear system 124 may rotate up to 360°. In a variation, the planetary gear system 124 may rotate less than 360°. In a variation, the planetary gear system 124 may rotate less than or equal to 180°. In a variation, the planetary gear system 124 may rotate less than or equal to 90°. In a variation, the planetary gear system 124 may rotate less than or equal to 45°. In some examples, the planetary gear system 124 may rotate 45°-90°, 90°-180°, or 180°-360°.

Figure 6D:
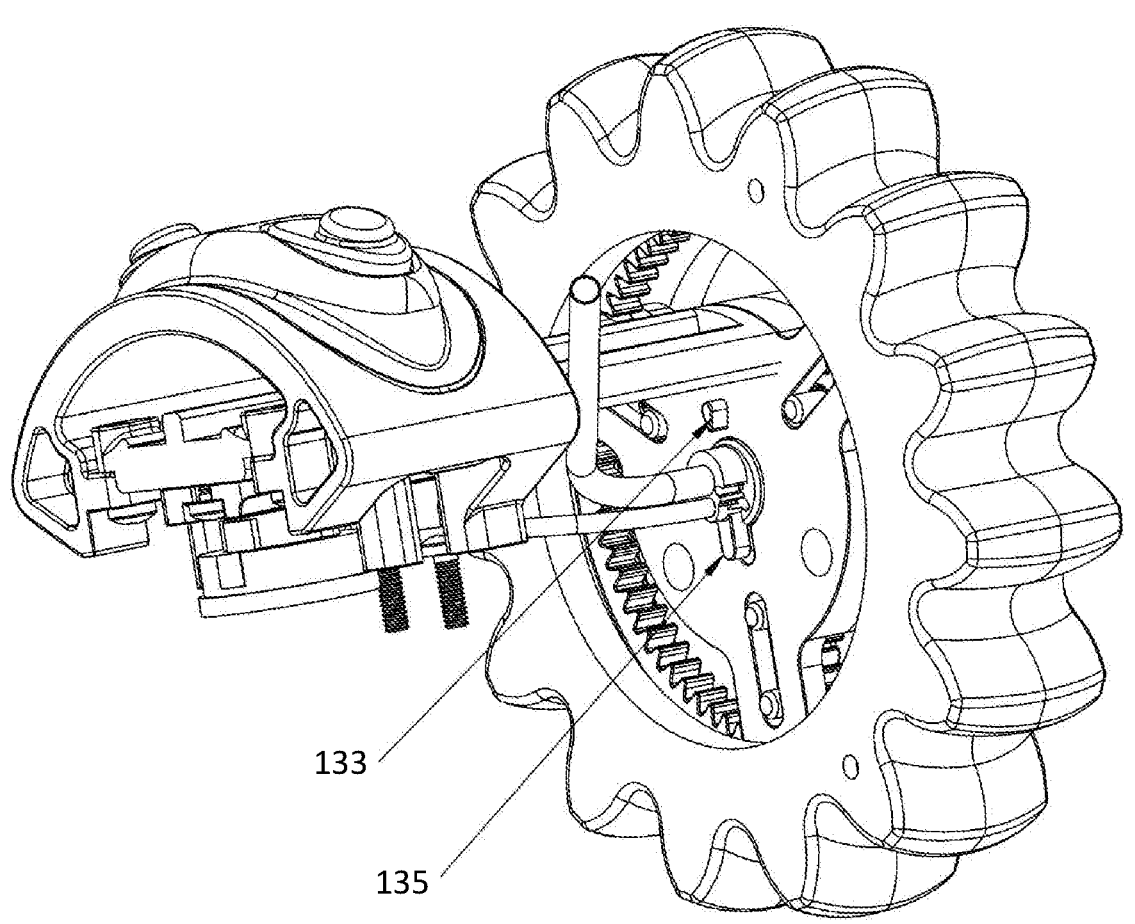
FIG. 6D is a view of the slider mechanism with rotational stops in the rotation assembly in one variation.

The planetary gear system may further include stops for preventing further rotation of the gears in one direction. This may prevent or reduce bending or restriction of the lumina/catheter as the rotation assembly is rotated. In some variations, the stops may include one or more fixed stops 133 and a rotating stop 135, for example, as seen in FIG. 6D. When the rotating stop 135 contacts the fixed stop 133, the planetary gear system 124 is prevented from rotating further in that direction. In a variation, the planetary gear system 124 may include one stop and may rotate up to 180° in a single direction (ex. ±180°). In a variation, the planetary gear system 124 may include two stops and may rotate up to 90° in a single direction (ex. ±90°). In a variation, the planetary gear system 124 may include three stops and may rotate up to 45° in a single direction (ex. ±45°). The number of stops may depend on the number of pull wires included for the catheter tip deflection. For example, the number of stops in the planetary gear system may be less than or equal to the number of pull wires used for the catheter tip deflection.

The planetary gear system 124 may increase or decrease rotation from the knob to the catheter at a ratio ranging from 4:1 to 1:4. Using a ratio for increased rotation allows for smaller rotations of the knob to translate to larger rotations of the catheter for ease of use and minimizing movement, allowing for one hand manipulation of the device. In a variation, the planetary gear system 124 may increase rotation from the knob to the catheter at a 4:1 ratio. In a variation, the planetary gear system 124 may increase rotation from the knob to the catheter at a 3:1 ratio (ex. 120° of knob rotation equals 360° of catheter rotation). In a variation, the planetary gear system 124 may increase rotation from the knob to the catheter at a 2:1 ratio. In a variation, the planetary gear system 124 may match rotation from the knob to the catheter at a 1:1 ratio. Using a ratio for decreased rotation allows for larger rotations of the knob to translate to smaller rotations of the catheter for improved resolution or sensitivity. In a variation, the planetary gear system 124 may decrease rotation from the knob to the catheter at a 1:2 ratio. In a variation, the planetary gear system 124 may decrease rotation from the knob to the catheter at a 1:3 ratio. In a variation, the planetary gear system 124 may decrease rotation from the knob to the catheter at a 1:3 ratio. In a variation, the planetary gear system 124 may decrease rotation from the knob to the catheter at a 1:4 ratio.

In a variation, the sun gear may be located inside the cylindrical body and the ring gear may be located outside the cylindrical body. The arms of the carrier may then extend through corresponding openings in the cylindrical body to connect the planet gears to the sun and ring gears. This arrangement allows for the slider mechanism to be pushed up and down the cylindrical body in a linear motion and still transfer rotary motion from the outside to the inside of the tube assembly. In some variations, the knob is integral with or connected to the planetary gear system. The inner surface of the knob may engage the planetary gear system and the outer surface of the knob may allow for the user to adjust or manipulate the planetary gear system. For example, the planetary gear system may include a ring gear on the inner surface of the knob, as seen in FIG. 6A and FIG. 6C. Therefore, a user may rotate the knob to effect rotation of the sun gear and anything attached to the sun gear, such as a catheter.

As seen in FIG. 6A, the outer surface of the knob 122 may include at least one recession 136 for receiving a finger or thumb of the user. The recession may aid the user in gripping the knob and the endoscopic device. The recession may also provide orientation for the positioning of the catheter. In other variations, the knob comprises a plurality of recessions on the outer surface of the knob. In some variations, the knob may include at least 1 recession along the circumference of the outer surface of the knob. In a variation, the knob may include at least 2 recessions. In a variation, the knob may include at least 3 recessions. In a variation, the knob may include at least 4 recessions. In a variation, the knob may include at least 5 recessions. In a variation, the knob may include at least 6 recessions. In a variation, the knob may include at least 10 recessions. In a variation, the knob may include at least 15 recessions along the circumference of the outer surface of the knob. In one variation, the at least one recession is about the width of an average thumb.

The slider mechanism 104 is also configured to translate toward the distal end or toward the proximal end of the cylindrical body 110. The translation of the slider mechanism provides for advancement or retraction of a catheter connected to the slider mechanism. The slider mechanism is able to translate along the cylindrical body because the openings 112 on the cylindrical body 110 extend the length of the cylindrical body and align with the arms 134 of the carrier 132 in the rotation assembly 106. Therefore, by way of the openings, the planet gears can engage with the ring gear on the inner surface of the knob while also allowing the entire slider mechanism to translate. In some variations, the slider mechanism may be moved along the length of the cylindrical body without rotating the rotation assembly. In other variations, the slider mechanism may be moved along the length of the cylindrical body while rotating the rotation assembly.

Figures 5A, 5B:
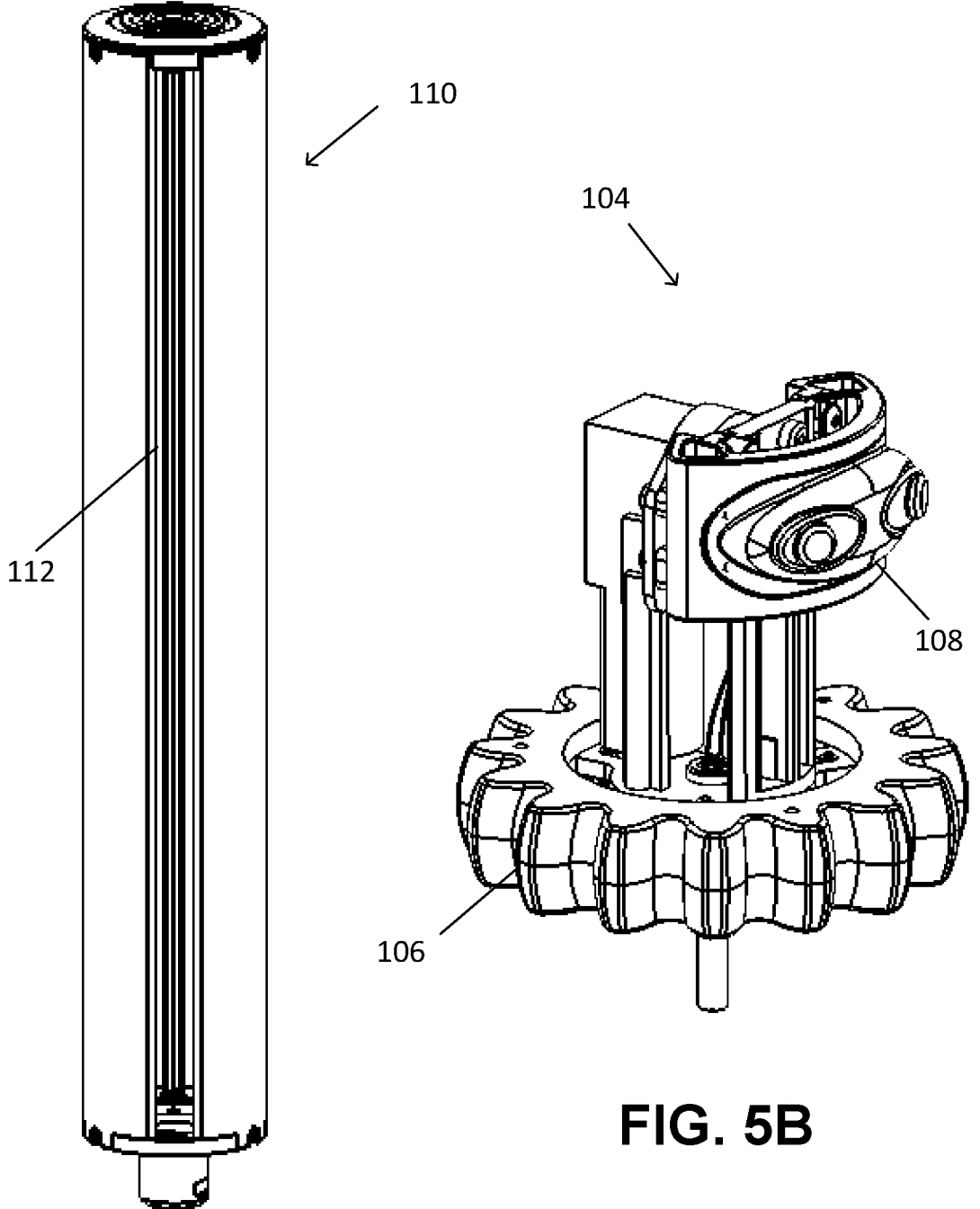
FIG. 5A is a view of the cylindrical body in one variation.
FIG. 5B is a view of the slider mechanism in one variation.

As seen in FIG. 5B, the slider mechanism 104 further includes a tip deflecting mechanism 108. The tip deflecting mechanism 108 is operatively connected to the rotation mechanism 106 such that both the tip deflecting mechanism and the rotation mechanism translate and rotate together. The tip deflecting mechanism allows for deflecting the distal tip of a catheter connected to the slider mechanism. In a variation, the tip deflecting mechanism may control a single pull wire operably connected to the distal tip of the catheter such that engaging the tip deflecting mechanism pulls the pull wire and moves or deflects the tip in a single direction. In another variation, the tip deflecting mechanism may control two pull wires operably connected to the distal tip of the catheter such that engaging the tip deflecting mechanism pulls a pull wire and moves or deflects the tip in up to two directions. In another variation, the tip deflecting mechanism may control three pull wires operably connected to the distal tip of the catheter such that engaging the tip deflecting mechanism pulls a pull wire and moves or deflects the tip in up to three directions.

The tip deflecting mechanism may include but is not limited to a switch, a lever, or at least one button. In a variation, a lever tip deflecting mechanism may have at least a first position corresponding to the catheter tip in a straight configuration and a second position corresponding to the catheter tip in a deflected configuration. In a variation, a switch tip deflecting mechanism may have at least a first position corresponding to the catheter tip in a straight configuration and a second position corresponding to the catheter tip in a deflected configuration. In a variation, a button tip deflecting mechanism may have at least a first button corresponding to the catheter tip in a straight configuration and a second button corresponding to the catheter tip in a deflected configuration. In some variations, the tip deflecting mechanism may include at least one button, at least two buttons, or at least three buttons.

In a variation, the tip deflecting mechanism may be non-powered. For example, the tip deflecting mechanism may be mechanically operated. The tip deflecting mechanism may be a non-powered lever. In another variation, the tip deflecting mechanism may be powered or motorized. For example, the tip deflecting mechanism may include gearing and a power source or access to a power source. In some examples, the power source for the motor for the tip deflecting mechanism may be within a control assembly, either integrated with or external to the tube assembly. A powered tip deflecting mechanism may provide more control and precise movement of the wire and therefore provide more control and precise movement of the distal tip of the catheter. The tip deflecting mechanism may be a powered lever, powered switch, or powered button. The tip deflecting mechanism may further include a sensor configured to measure the degree of deflection of the tip of the catheter. The sensor may be configured to determine the location of the distal tip or how much the distal tip has deflected in relation to a straight configuration. For example, the sensor may measure the movement of gears in a powered tip deflecting mechanism that may then be converted to the movement of the distal tip of the catheter. In a variation, the tube assembly may further include an indicator operatively connected to the sensor to provide information on the location of the distal tip of the catheter or the amount of change in the deflection of the distal tip. In one variation, the indicator may be a display.

Figure 8A:
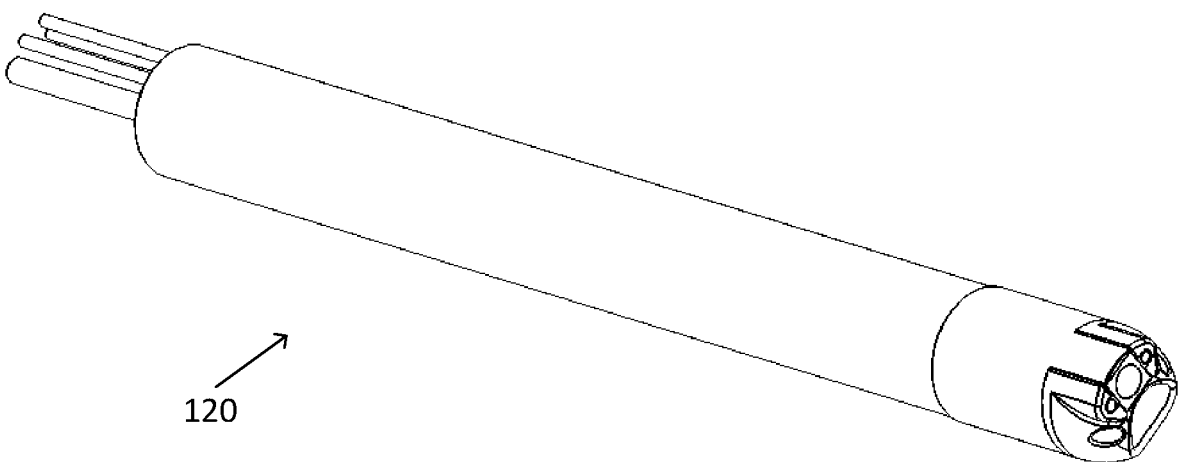
FIG. 8A is a view of the catheter in one variation.

The endoscopic device 100 may further include a catheter 120 operatively connected to the slider mechanism 104. In a variation, the distal end of the catheter may then be manipulated by operation of the slider mechanism. In a variation, the catheter may include at least two lumina that extend longitudinally along the catheter. FIG. 8A shows a portion of the catheter 120 and FIGS. 8B-8F show various cross-sections of the catheter 120. In a variation, the catheter may include at least three lumina that extend longitudinally along the catheter. In a variation, the catheter may include at least four lumina that extend longitudinally along the catheter. In a variation, the catheter may include at least five lumina that extend longitudinally along the catheter.

Referring to FIGS. 3A and 3B, the tube assembly 102 may further include one or more ports fluidly connected to the catheter (not shown). The tube assembly 102 may include at least one port, at least two ports, or at least three ports fluidly connected to the catheter. In some variations, the ports may be connected to the slider mechanism 104 such that the ports also translate when the slider mechanism 104 is translated along the cylindrical body 110. The ports may provide access to one or more lumina of the catheter. In some variations, the ports may be flush ports 137 connected to one or more lumina for irrigation. The flush ports 137 may be configured for connecting to a source of irrigation fluid, such as saline. In some variations, the ports may be access ports 139 connected to one or more lumina for working channel access. In a variation, the tube assembly includes two flush ports. In another variation, the tube assembly includes a flush port 137 and a working channel access port 139. In some examples, the tube assembly 102 may include may include two ports at the same location on the tube assembly via a Y-connector 138, as seen in FIG. 3A, or may include two ports separated by a distance along the tube assembly, as seen in FIG. 3B. FIG. 3A shows a Y-connector 138 with catheter ports for fluidly accessing the lumina of the catheter 120 attached to the slider mechanism 104 on the tube assembly 102. In one variation, the Y-connector 138 and/or ports may extend though one of the plurality of openings on the cylindrical body 110.

As seen in FIGS. 8B-8F, the lumina may be irrigation channels, pull wire channels, electrical channels, and/or a working channel. For example, the catheter 120 may include at least one or at least two irrigation channels 140, at least one electrical channel 141, at least one working channel 142, and at least one pull wire channel 143. The irrigation channels 140 may be used to supply fluid to the distal end of the catheter. The electrical channel(s) 141 may be used to hold connections for a camera and/or light source at the distal end of the catheter. The working channel may be used to provide access to the distal end of the catheter. Therapeutic devices, diagnostic devices, or accessories may be passed through the working channel for use at the distal end of the catheter. The working channel can also be used to aspirate and/or flush fluid in or out of the catheter. The pull wire channels may be used to hold one or more pull wires for manipulating the deflection of the catheter. In a variation, the catheter may include at least one pull wire channel. In another variation, the catheter may include at least two pull wire channels. In another variation, the catheter may include at least three pull wire channels. When more than one pull wire channels are present, they may be located opposite one another and/or equidistant from one another to allow for greater control of the deflection of the catheter tip.

Figure 8B:
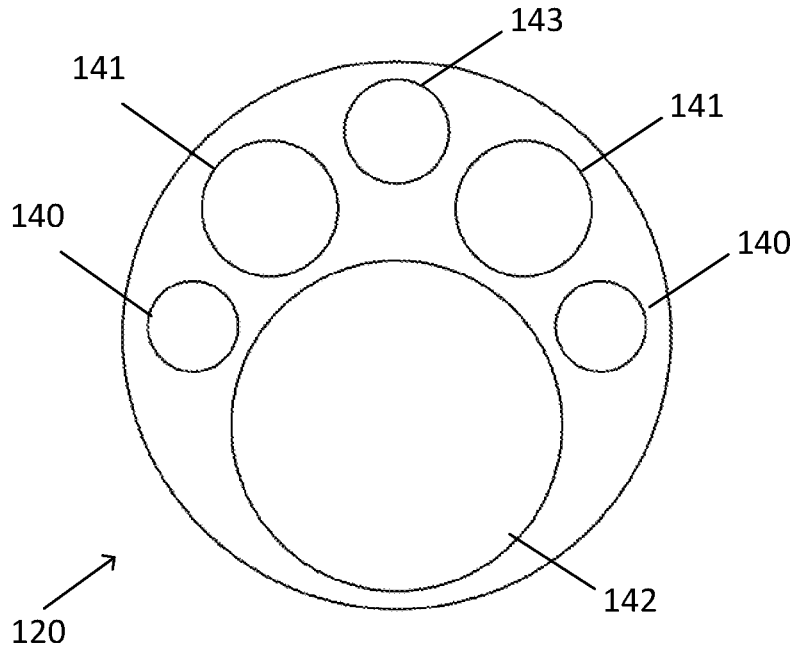
FIG. 8B is a cross-sectional view of the catheter in one variation.
Figure 8C:
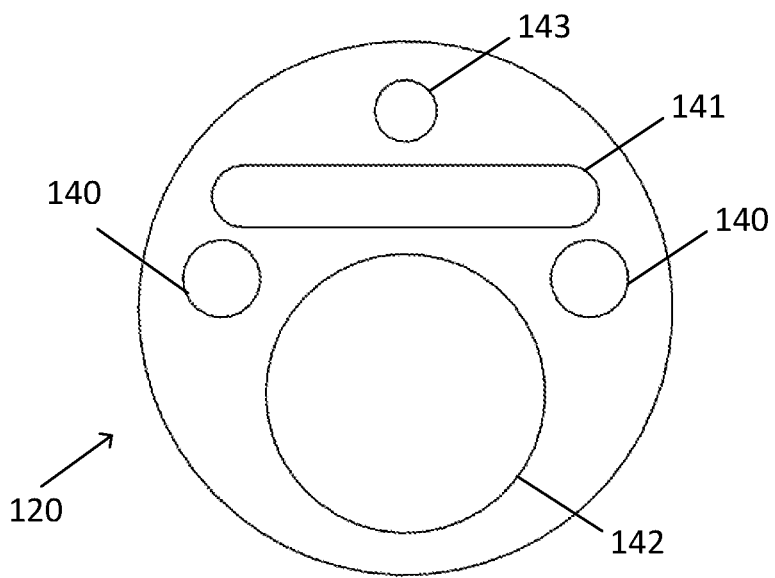
FIG. 8C is a cross-sectional view of the catheter in one variation.
Figure 8D:
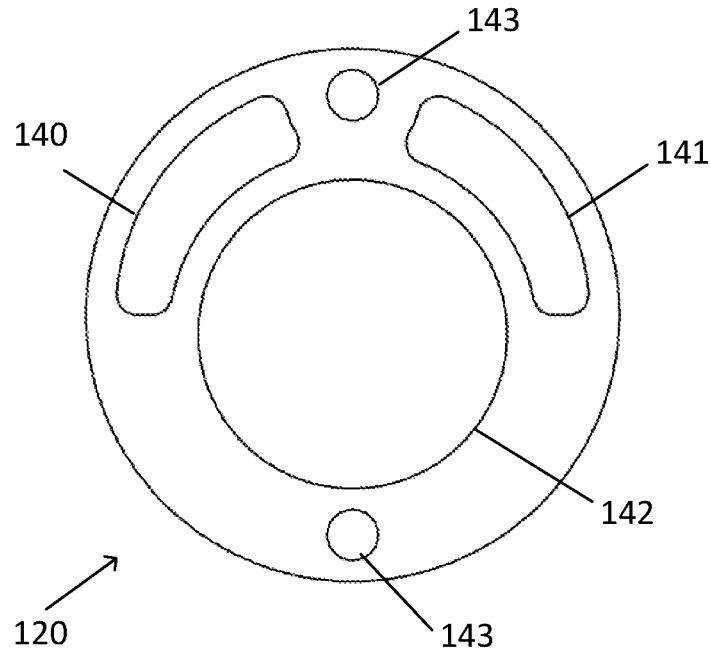
FIG. 8D is a cross-sectional view of the catheter in one variation.
Figure 8E:
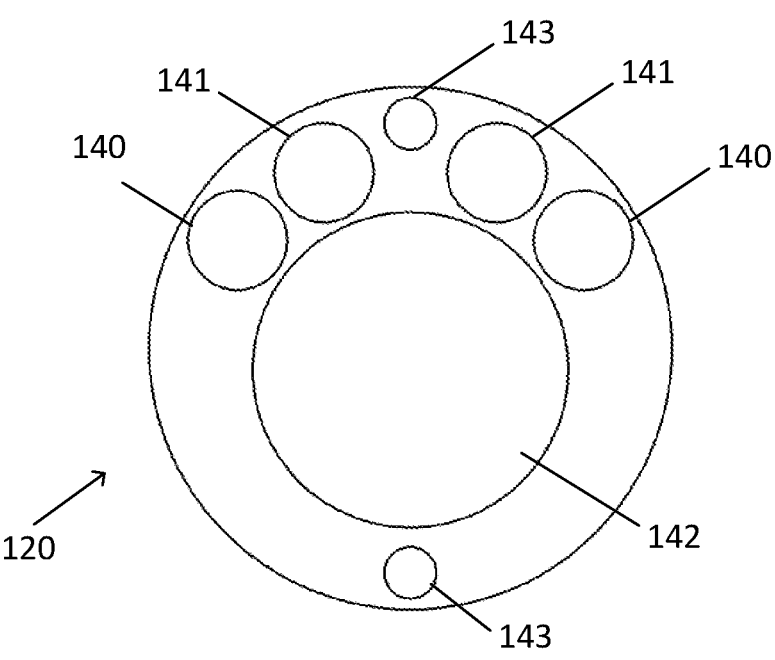
FIG. 8E is a cross-sectional view of the catheter in one variation.
Figure 8F:
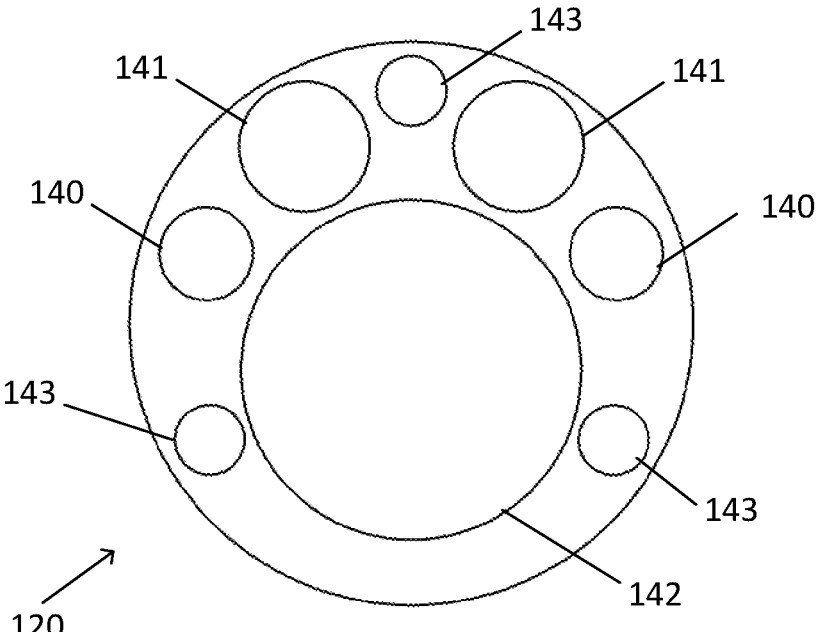
FIG. 8F is a cross-sectional view of the catheter in one variation.

As seen in FIG. 8B, in at least one variation, the catheter 120 may include two irrigation channels 140, two electrical channels 141, a working channel 142, and one pull wire channel 143. As seen in FIG. 8C, in at least one variation, the catheter 120 may include two irrigation channels 140, one electrical channel 141, a working channel 142, and one pull wire channel 143. In this variation, the one electrical channel 141 may be slotted such that it has an oval cross-sectional shape and may be configured to hold connections for both the camera and light source(s). As seen in FIG. 8D, in at least one variation, the catheter 120 may include one irrigation channel 140, one electrical channel 141, a working channel 142, and two pull wire channels 143. In this variation, the irrigation channel 140 and the electrical channel 141 are slotted and curved in shape. As seen in FIG. 8E, in at least one variation, the catheter 120 may include two irrigation channels 140, two electrical channels 141, a working channel 142, and two pull wire channels 143. As seen in FIG. 8F, in at least one variation, the catheter 120 may include two irrigation channels 140, two electrical channels 141, a working channel 142, and three pull wire channels 143.

Figure 8G:
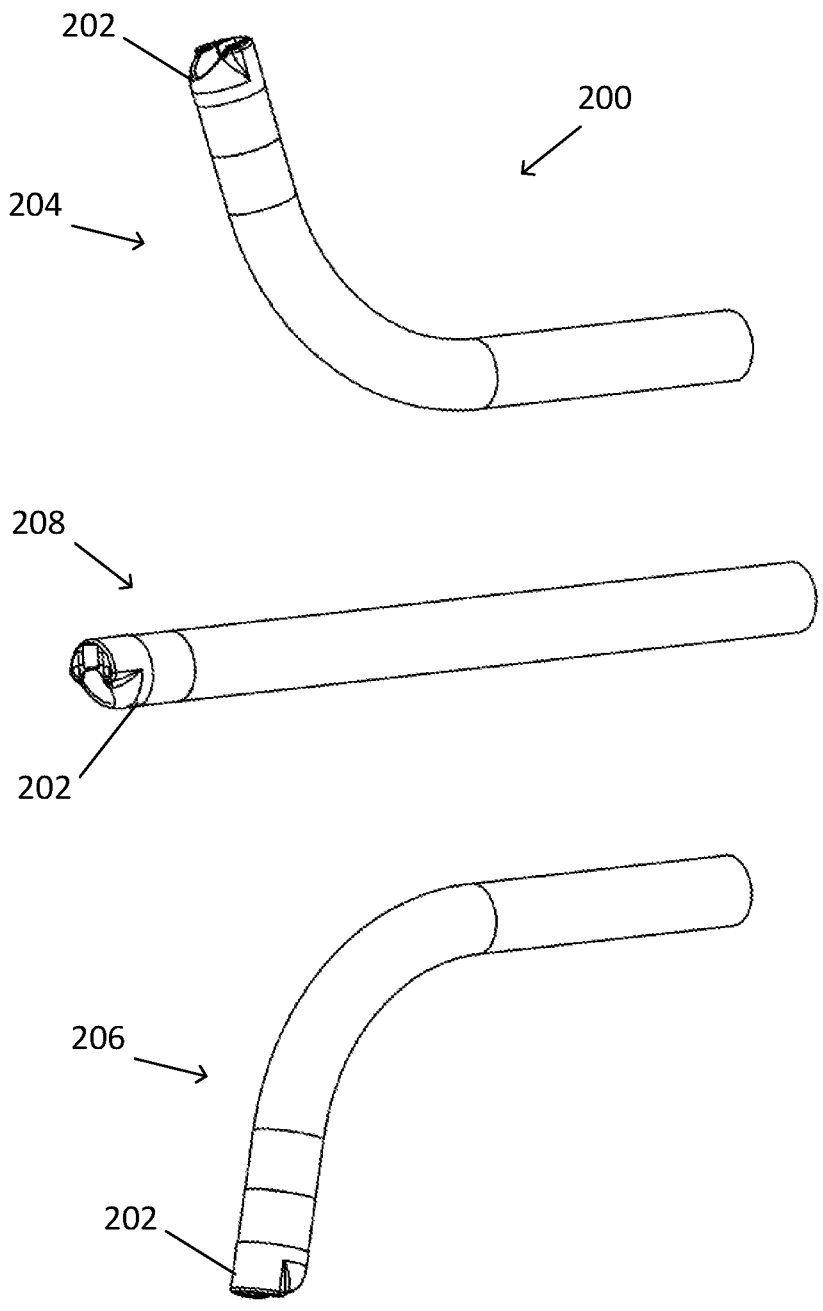
FIG. 8G depicts a catheter with a preformed distal end (i.e., tip).

FIG. 8G depicts a catheter 200 with a preformed distal end (i.e., tip) 202. As depicted in FIG. 8G, the distal end is preformed to be in a set position 204, in this case perpendicular (90 degrees) to the central axis of the catheter. With no tension from the pull wire, the preformed distal end 202 remains at 90 degrees. When tension is applied via the tip deflecting mechanism and pull wire, the distal end 202 can be deflected in the opposite direction, i.e. up to −90 degrees. In some variations, the distal end 202 may be deflected up to −90 degrees in the opposite direction (position 206). In other variations, the distal end 202 may be defected to be in line with the central axis of the catheter (position 208). Using a catheter with a preformed distal end may allow for the distal end to deflect ±90 degrees using one pull wire. It will be appreciated that 90 degrees is only for illustration; the preformed set position can be at any angle from 0-180 degrees.

The size and shape of the lumina in the catheter may vary depending on the number of lumina and the arrangement within the catheter. For example, the lumina may have a circular, oval, square, rectangular, curved, star-shaped, or irregular cross-sectional shape. Different lumina for electrical channels, working channel, and/or irrigation channels can have different shapes or the same shapes. The addition of one or more pull wire channels may change the size of the electrical channels, working channel, and/or irrigation channels. In a variation, the working channel may have a diameter of greater than 1.5 mm. In a variation, the working channel may have a diameter of at least 1.8 mm. In a variation, the working channel may have a diameter of at least 1.9 mm. In a variation, the working channel may have a diameter of at least 2 mm. For example, the working channel may be 20%-50% larger than a working channel in a standard endoscopic device (usually 1.2 mm). In a variation, the working channel may be 20% larger that a working channel in a standard endoscopic device. In a variation, the working channel may be 30% larger that a working channel in a standard endoscopic device. In a variation, the working channel may be 40% larger that a working channel in a standard endoscopic device. In some variations, the endoscopic device is a cholangioscope. In a variation, the working channel may be 50% larger that a working channel in a standard endoscopic device. In a variation, the working channel may be 60% larger that a working channel in a standard endoscopic device. In a variation, the working channel may be 70% larger that a working channel in a standard endoscopic device. A larger working channel may allow for larger and a wider variety of therapeutic and diagnostic devices or accessories to be placed within the working channel. The working channel 142 may provide for access for therapeutic probes at the tip of the catheter including, but not limited to forceps, laser probes, Electro-hydraulic Lithotripsy (EHL) probes, or Radiofrequency Ablation (RFA) probes. In one example, the working channel of a catheter used with a cholangioscope may be about 50% larger than the working channel on standard cholangioscope catheters (i.e. SpyGlass™). The larger working channel may have capacity for 60% larger biopsy forceps or provide improved suction for ductal clearance.

The catheter 120 may have an outer diameter of at least 3 mm. In a variation, the catheter may have a diameter of at least 3.5 mm. In a variation, the catheter may have a diameter of at least 4 mm. In a variation, the catheter may have a diameter of at least 4.5 mm. In a variation, the catheter may have a diameter of at least 5 mm. In other variations, the catheter size may range from about 5 French to about 15 French. In a variation, the catheter may have a diameter of at least 5 French. In a variation, the catheter may have a diameter of at least 7 French. In a variation, the catheter may have a diameter of at least 10 French. In a variation, the catheter may have a diameter of at least 11 French. In a variation, the catheter may have a diameter of at least 13 French. In a variation, the catheter may have a diameter of at least 15 French. In another variation, the catheter may have a diameter of less than or equal to 10 French. The size of the catheter may be selected based on the use of the endoscopic device and where it will be used in the body.

Figure 9A:
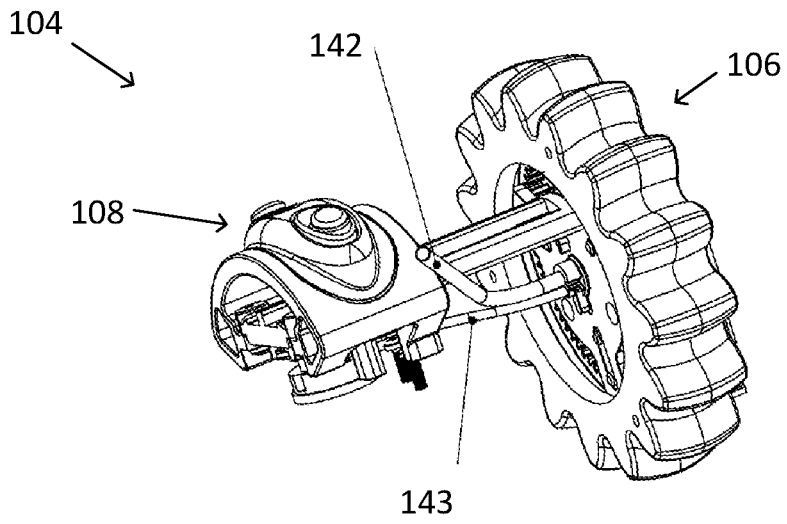
FIG. 9A is a view of the slider mechanism with lumens in one variation.
Figure 9B:
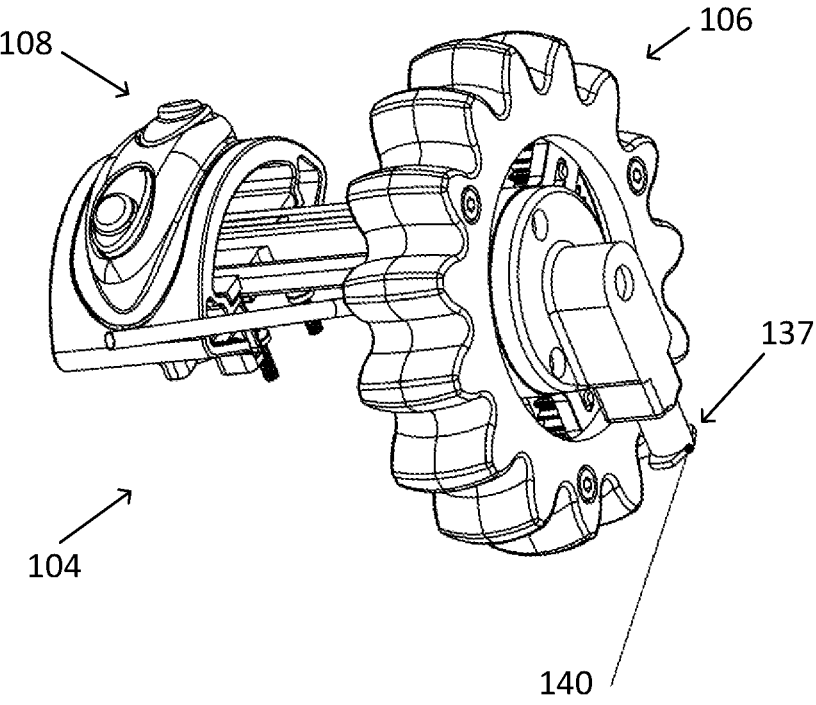
FIG. 9B is a view of the slider mechanism with lumens in one variation.

Referring to FIGS. 9A and 9B, one or more of the lumina of the catheter may connect to or extend through the slider mechanism 104 for connection to the one or more ports or the tip deflecting mechanism 108. For example, FIG. 9A shows the working channel 142 and a pull wire channel 142 passing through the rotation assembly 106. In a variation, the working channel 142 may terminate in a working channel access port (not shown). In another variation, the pull wire channel 143 may be connected to the tip deflecting mechanism 108 such that the pull wire in the pull wire channel 143 may be controlled by the tip deflecting mechanism 108. In another example, FIG. 9B shows an irrigation channel 140 connected to the rotation assembly 106. In a variation, the irrigation channel 140 may terminate in a flush port 137.

Figure 10A:
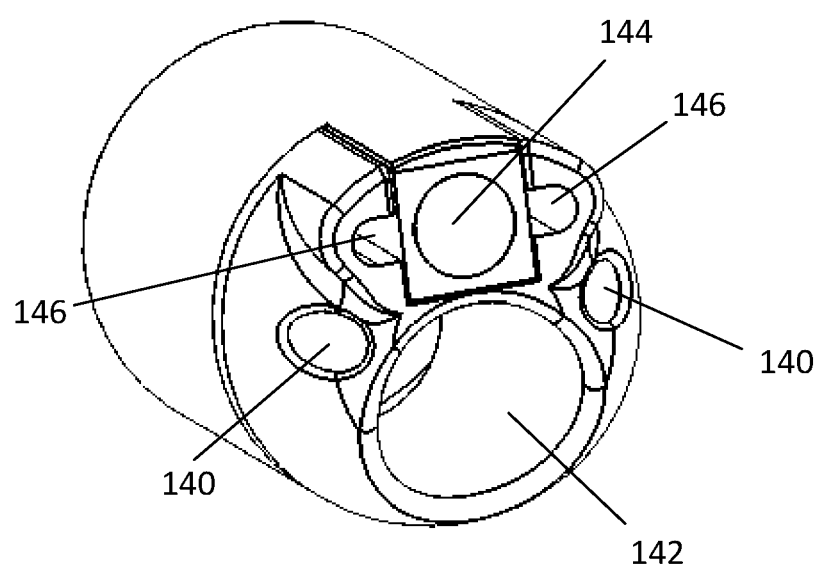
FIG. 10A is a view of the distal tip of the catheter in one variation.
Figure 10B:
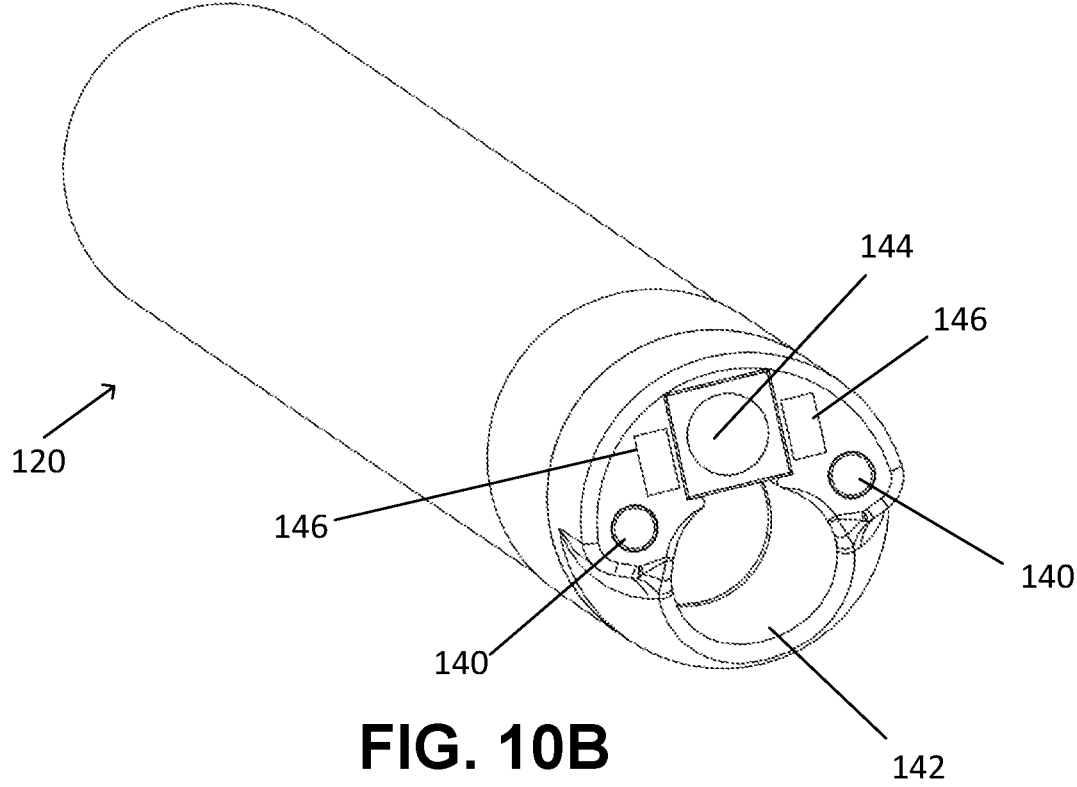
FIG. 10B is a view of the distal tip of the catheter in one variation.

Referring to FIGS. 10A and 10B, the catheter 120 may further include a camera 144 at the distal end of the catheter. The camera 144 may be connected to the tube assembly 102. In an example, the camera 144 may be connected to an electrical channel 141 in the catheter 120. The camera 144 may receive power and/or send signals through the electrical channel 121. In a variation, the camera may be a CMOS camera. The camera may have a resolution of at least 100,000 pixels. In a variation, the camera may have a resolution of at least 120,000 pixels. In a variation, the camera may have a resolution of at least 140,000 pixels. In a variation, the camera may have a resolution of or at least 160,000 pixels. In a variation, the camera may have a field of view of at least 100°. In a variation, the camera may have a field of view of at least 110°. In a variation, the camera may have a field of view of at least 120°. The camera may provide for enhanced visual inspection of benign and malignant neoplasms and may improve diagnostic capabilities of the endoscopic device. Better visualization provided by the camera in the catheter may improve therapeutic interventions provided by the endoscopic device.

In a variation, the catheter 120 may further include a light source 146 at its distal end to provide light for the camera 144. The catheter may include at least one light source or at least two light sources. In one variation, the light source may be an LED located at the distal end of the catheter. In another variation, the light source 146 may be two LEDs at the distal end of the catheter, as seen in FIGS. 10A and 10B. The LEDs may be circular or rectangular in shape and may be located on either side of the camera 144. In a variation, the light source may be at least one LED recessed from the distal end of the catheter, such that the LEDs and the camera are not located on the same plane. For example, the LED may be a distance from the distal end of the catheter and the distal end of the catheter may be translucent such that the translucent distal end disperses the light from the LED and causes the distal end of the catheter to glow. In another variation, the catheter may include at least one optical fiber that that transmits light from a light source external to the catheter to the distal end of the catheter. For example, the light source may be in the control assembly or may be external to the endoscopic device and the light signal transmitted through an optical fiber.

The endoscopic device 100 may be used for flexible gastrointestinal endoscopy. Non-limiting examples of endoscopic devices include a laryngoscope, an esophagoscope, esophagogastroduodenoscope, an enteroscope, a colonoscope, a duodenoscope, a cholangioscope, a rectoscope, or a proctoscope. In one variation, the endoscopic device is a cholangioscope. In one example, the cholangioscope may be used in endoscopic retrograde cholangiopancreatography (ERCP) or intraductal endoscopy and cholangiopancreatography (IECP). The endoscopic device may or may not include video imaging capabilities.

As seen in FIGS. 2 and 8, the endoscopic device 100 may further include a control assembly 116. In a variation, the control assembly 116 may include a microprocessor. For example, the microprocessor may be a video processor. The video processor may be operatively connected to the camera in the catheter. The video processor may be configured to process a video signal from the camera to be transmitted for viewing. The video signal may be transmitted to a display for viewing via a wire or wirelessly. In a variation, the control assembly 116 also includes a wireless transceiver. In some variations, the wireless transceiver may be a WiFi or Bluetooth transceiver. The wireless transceiver may be configured to send and/or receive signals, such as video signals. In other variations, the control assembly may include a WiFi or Bluetooth transmitter. In one variation, the wireless transceiver may be configured to send the video signal from the video processor to a video display. The transmission of the video signal may be simultaneous with the operation of the endoscopic device, such that an operator of the endoscopic device can view the location of the distal end of the catheter in real time. In other variations, the video processor may be connected to a display via a wire or cable.

In some variations, the control assembly 116 also includes a light source. The light signal from the light source in the control assembly may then be transmitted to the distal end of the catheter with optical fibers. In other variations, the light source may be at the distal end of the catheter or may be located external to the endoscopic device. In some variations, the control assembly 116 may further include a power source. For example, the power source may be a battery. The battery may be disposable or rechargeable. In other variations, the control assembly may be powered by an external power source. For example, the control assembly may be powered through a USB connection. The control assembly may also be connected to an endoscope attachment 118. The endoscope attachment 118 may be configured to fit within a portion of the working channel of a larger endoscope The control assembly and the tube assembly may be fluidly connected such that a catheter may pass through the control assembly and into the tube assembly. In a variation, the tube assembly 102 and the control assembly 116 may be detachably connected. For example, as seen in FIG. 2, the tube assembly 102 and the control assembly 116 may be connected with a locking mechanism 114. In this variation, one or both of the tube assembly and control assembly may be disposable. In another variation, the tube assembly and the control assembly are integrally connected as a single assembly. For example, the tube assembly and the control assembly may not be separated. In another variation, the control assembly may be located within the tube assembly. When the tube assembly and the control assembly are integrally connected, the tube assembly and the control assembly are both single use/disposable. The inclusion of the control assembly in the endoscopic device provides for a clinician to use the device without requiring capital equipment. For example, the endoscopic device may include an integrated microprocessor, light source, and or power source which eliminates the need for endoscopic capital equipment. This may allow clinicians greater access to the endoscopic device because they do not need to invest in capital equipment in order to operate the endoscopic device. Instead, all the equipment needed is included in the endoscopic device. Moreover, the single use aspect of the endoscopic device may prevent contamination between patients. In another variation, the control assembly is separate from and external to the tube assembly. For example, the control assembly may be located in a separate box and may connect to the tube assembly and/or catheter using an accessory cable connection. The separate control assembly may be configured for processing/controlling a motor for tip deflection, the LEDs, and/or processing video and may be powered through USB or battery. In some examples, the separate control assembly may intercept the video signal for processing before the video signal goes to a monitor. The separation of the control assembly in the endoscopic device provides for a reduction in the size of the endoscopic device. In addition, a separate control assembly may be reused between patients. The separate control assembly may be smaller than standard endoscopy capital equipment and may be easily transported or moved between rooms, hospitals, or locations. This may allow clinicians greater access to the endoscopic device because they do not need to invest in large or expensive capital equipment in order to operate the endoscopic device.

Further provided herein is a method of manipulating the endoscopic device by inserting the endoscopic device with a catheter through a working channel of an endoscope. The method may further include rotating the rotation assembly around the cylindrical body to rotate the catheter of the endoscopic device. In some variations, the rotation assembly may rotate up to or including 360°. In some variations, the rotational assembly may rotate up to or including 180°. In some variations, the rotational assembly may rotate up to or including 90°. In some variations, the rotational assembly may rotate up to or including 60°. This can depend on the number of stops and/or pull wires, which can rotate the catheter up to or including 360°.

In some variations, the rotational assembly may rotate up to or including 200° clockwise and counterclockwise. In some variations, the rotational assembly may rotate up to or including 100° clockwise and counterclockwise. In some variations, the rotational assembly may rotate up to or including 70° clockwise and counterclockwise.

The method may further include translating the slider mechanism toward the distal end or toward the proximal end of the cylindrical body to extend or retract the catheter, respectively. The method may further include engaging a tip deflecting mechanism to deflect the tip of the catheter. The movement of the slider mechanism (rotation, advancement and/or retraction, and tip deflection) provides for intuitive, single handed manipulation of a catheter associated with the endoscopic device and provides greater control of the catheter over existing devices.

The method may further include activating a light source in the control assembly or at the distal tip of the catheter and acquiring a video signal from a camera at the distal tip of the catheter. The method may further include flushing the distal end of the catheter with an irrigation fluid. This may clear the area in front of the camera to provide a clearer video image. The method may further include processing the video signal from the camera with a video processor in a control assembly and transmitting the video signal to an external display. The video signal may be transmitted wirelessly using a wireless transceiver. The transmission of the video signal may allow the user to view the anatomy at the distal end of the catheter in real time. This may provide feedback for further manipulation of the catheter with the tube assembly of the endoscopic device.

It should be noted that the endoscopic device represents a single variation for endoscopy, and claimed subject matter is not limited to any particular variation. For example, an endoscopic device may be used in association with other endoscopic devices or catheter manipulation mechanisms and advanced into body cavities, including but not limited to the esophagus, colon, or biliary ducts of a human patient, animal patient. Other variations may involve the use of other types of probing devices that may be used to view or probe objects in internal structures of living organisms and/or mechanical apparatuses, and the claimed subject matter is not limited in this respect.

Having described several variations, it will be recognized by those skilled in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Those skilled in the art will appreciate that the presently disclosed variations teach by way of example and not by limitation. Therefore, the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. An endoscopic device comprising:
a tube assembly comprising:
    a cylindrical body having a proximal end and a distal end and comprising a plurality of openings extending from the proximal end to the distal end of the cylindrical body; and
    a slider mechanism connected to the cylindrical body and configured to translate along the cylindrical body toward the distal end or toward the proximal end of the cylindrical body to provide for advancement or retraction, respectively, of an associated catheter operatively connected to the slider mechanism, the slider mechanism comprising:
        a rotational assembly configured to provide for rotation of the associated catheter; and a tip deflecting mechanism configured to provide for deflection of a tip of the associated catheter, the tip deflecting mechanism operatively connected to the rotational assembly such that both the tip deflecting mechanism and the rotational assembly are configured to translate and rotate together relative to the cylindrical body,
    wherein the slider mechanism is configured to rotate at least 360° around the cylindrical body.

2. The endoscopic device of claim 1, wherein the rotational assembly comprises a planetary gear system.

3. The endoscopic device of claim 2, wherein the rotation assembly further comprises a knob having an outer surface and an inner surface.

4. The endoscopic device of claim 3, wherein the planetary gear system comprises a ring gear on the inner surface of the knob.

5. The endoscopic device of claim 2, wherein the planetary gear system comprises at least two planet gears.

6. The endoscopic device of claim 3, wherein the knob comprises a plurality of recessions on the outer surface of the knob.

7. The endoscopic device of claim 3, wherein the planetary gear system increases or decreases rotation from the knob to the associated catheter at a ratio ranging from 4:1 to 1:4.

8. The endoscopic device of claim 1, wherein the slider mechanism is configured to rotate up to and including 200° around the cylindrical body in a clockwise direction and up to and including 200° around the cylindrical body in a counterclockwise direction.

9. The endoscopic device of claim 1, wherein the tube assembly further comprises at least two ports configured to be fluidly connected to the associated catheter.

10. The endoscopic device of claim 1, wherein the endoscopic device is a cholangioscope.

11. The endoscopic device of claim 1, further comprising a control assembly comprising a video processor.

12. The endoscopic device of claim 11, wherein the control assembly further comprises an endoscope attachment configured to connect the endoscopic device to a larger endoscope by aligning an entry port of the larger endoscope with a working channel of the endoscopic device.

13. The endoscopic device of claim 11, wherein the control assembly further comprises a light source.

14. The endoscopic device of claim 11, wherein the control assembly further comprises a wireless transceiver.

15. The endoscopic device of claim 11, wherein the control assembly further comprises a battery.

16. The endoscopic device of claim 1, wherein the tip deflecting mechanism is a switch, a lever, or at least one button.

17. The endoscopic device of claim 1, wherein the tip deflecting mechanism is powered.

18. The endoscopic device of claim 11, wherein the tube assembly and the control assembly are detachably connected with a locking mechanism.

19. The endoscopic device of claim 11, wherein the tube assembly and the control assembly are integrally connected.

20. A method of manipulating the endoscopic device of claim 1, the method comprising:
    inserting the endoscopic device comprising the associated catheter through a working channel of an endoscope.

21. The method of claim 20, further comprising rotating the rotational assembly around the cylindrical body to rotate the associated catheter of the endoscopic device.

22. The method of claim 20, further comprising translating the slider mechanism toward the distal end or toward the proximal end of the cylindrical body to advance or retract the associated catheter, respectively.

23. The method of claim 20, further comprising engaging the tip deflecting mechanism, wherein the tip deflecting mechanism is a switch, a lever, or at least one button.

24. The method of claim 23, wherein the tip deflecting mechanism is powered.

25. The method of claim 20, wherein the endoscopic device further comprises a control assembly, the method further comprising:

activating a light source in the control assembly and acquiring a video signal from the tip of the associated catheter.

26. The method of claim 25, further comprising processing the video signal with a video processor and transmitting the video signal to an external display.

27. The method of claim 26, further comprising transmitting the video signal wirelessly using a wireless transceiver.

28. The endoscopic device of claim 1, wherein the tip deflecting mechanism is connected to the tip of the associated catheter by a single pull wire, and wherein the tip deflecting mechanism is configured to provide for deflection of the tip of the associated catheter by pulling the single pull wire.

* * * * *